United States Patent [19]

Church et al.

[11] Patent Number: 5,202,016
[45] Date of Patent: Apr. 13, 1993

[54] STREAMING CURRENT DETECTOR WITH HEAD-CREATING PASSAGEWAY AND FLUID TREATMENT SYSTEM USING SAME

[75] Inventors: Garry Church, Beverley; Graham R. Willard, Hull, both of England

[73] Assignee: Lasertrim Limited, Hull, England

[21] Appl. No.: 573,854

[22] Filed: Aug. 28, 1990

[30] Foreign Application Priority Data

Aug. 29, 1989 [GB] United Kingdom ................ 8919513

[51] Int. Cl.⁵ ..................... B01D 35/00; B01D 37/03; G01N 27/60
[52] U.S. Cl. ................................. 210/85; 73/864.62; 210/96.1; 210/140; 210/143; 210/198.1; 210/709; 210/746; 324/71.1; 324/453
[58] Field of Search ................. 73/864.62; 137/453, 137/590; 210/85, 92, 93, 96.1, 143, 198.1, 192, 709, 745, 746, 87, 139, 140; 324/71.1, 453; 340/529, 825.15; 422/127, 128; 134/143, 184

[56] References Cited

U.S. PATENT DOCUMENTS

| | | | |
|---|---|---|---|
| 2,082,299 | 6/1937 | Nonhebel et al. | 137/590 |
| 3,262,878 | 7/1966 | Beckley et al. | 210/709 |
| 3,368,145 | 2/1968 | Gerdes | 324/453 |
| 3,399,133 | 8/1968 | Gerdes et al. | 324/453 |
| 4,070,617 | 1/1978 | Kachel et al. | 324/71.1 |
| 4,446,435 | 5/1984 | Canzoneri | 324/453 |
| 4,449,101 | 5/1984 | Canzoneri et al. | 324/453 |
| 4,535,285 | 8/1985 | Evans et al. | 324/71.1 |
| 4,769,608 | 9/1988 | Bryant | 324/453 |
| 4,855,061 | 8/1989 | Martin | 210/709 |

*Primary Examiner*—Robert A. Dawson
*Assistant Examiner*—Joseph Drodge
*Attorney, Agent, or Firm*—Hopgood, Calimafde, Kalil, Blaustein & Judlowe

[57] ABSTRACT

A device for detecting and monitoring the charge condition of finely divided solid charged particles in a fluid-flow is so devised as to accept the continuous and full volumetric flow of the fluid and to automatically and repeatedly sample and measure the charge condition. The full flow is accommodated without restriction in a passageway which intersects a bore wherein a streaming current detector (SCD), located below the passageway, is caused to cyclically sample and measure the charged-particle content of the flow; and at a passageway location downstream from the point point of cyclical sampling a head-creating formation assures that the fluid level will be raised to maintain a filled condition of the sampling bore. The device is further illustratively disclosed in use in a fluid-treatment system, wherein the SCD produces a signal to control flocculant added to the full flow of the fluid.

16 Claims, 4 Drawing Sheets

STREAMING CURRENT DETECTOR WITH HEAD-CREATING PASSAGEWAY AND FLUID TREATMENT SYSTEM USING SAME

BACKGROUND OF THE INVENTION

1. Field of the Invention

The present invention relates to a detection apparatus for monitoring the charge condition of a suspension of finely divided solid charged particles in a fluid, such as water. The results of the monitoring can be used for the control of a water treatment process, for example flocculation, the monitoring being carried out on the water after such treatment to provide a feedback control over the dosing with flocculant. The invention also relates to a fluid treatment system using such a detection apparatus.

2. Description of the Prior Art

It is well known to clarify different forms of process water containing various concentrations of suspended particles by a process of flocculation, in which the suspended finely divided particles are made to agglomerate together to form relatively large particles which can then be removed from the fluid medium by any one or more of a number of physical separation processes such as filtration, sedimentation etc. The process of flocculation involves the addition of a suitable flocculating chemical, chosen according to the known nature of the particles concerned. These chemicals have the effect of neutralising the normally charged particles, whereby the agglomeration of the particles is no longer inhibited by the forces of mutual repulsion which previously kept the particles separated. The success of the flocculation process relies heavily upon accurate control over the amount of flocculating chemical added to the suspension; if too little chemical is added charge neutralisation is incomplete, whereas the addition of too much chemical may cause reversal of the charges on the particles, resulting in the same fine division of the particle in the treated fluid as in the original untreated fluid. Moreover, over-dosing may result in further contamination of the fluid.

The traditional method of ensuring correct dosing was to test a number of samples of the untreated fluid with different amounts of the flocculating agent and to then proceed with the full-scale flocculating process employing a concentration equal to that giving optimum flocculation in the samples. It will be appreciated that this process was laborious, time consuming, and subject to inaccuracies when applied to a fluid medium flow with time-varying particulate concentration.

The need for a reliable instrument for accurate determination of particulate concentrations gave rise to a device which employs a phenomenon known as the streaming current effect, this device being known as a streaming current detector, and referred to herein as SCD. This effect involves the immobilisation of a layer of the charged particles on a surface and the rapid movement of further suspended particles over this layer, a resulting signal generated across electrodes spaced apart along the surface in the direction of particle movement having a magnitude dependent upon a number of factors, including the particle concentration. A number of instruments using the streaming current effect have been developed over recent years, one example being illustrated in FIG. 1 of the accompanying drawings.

Figure 1:
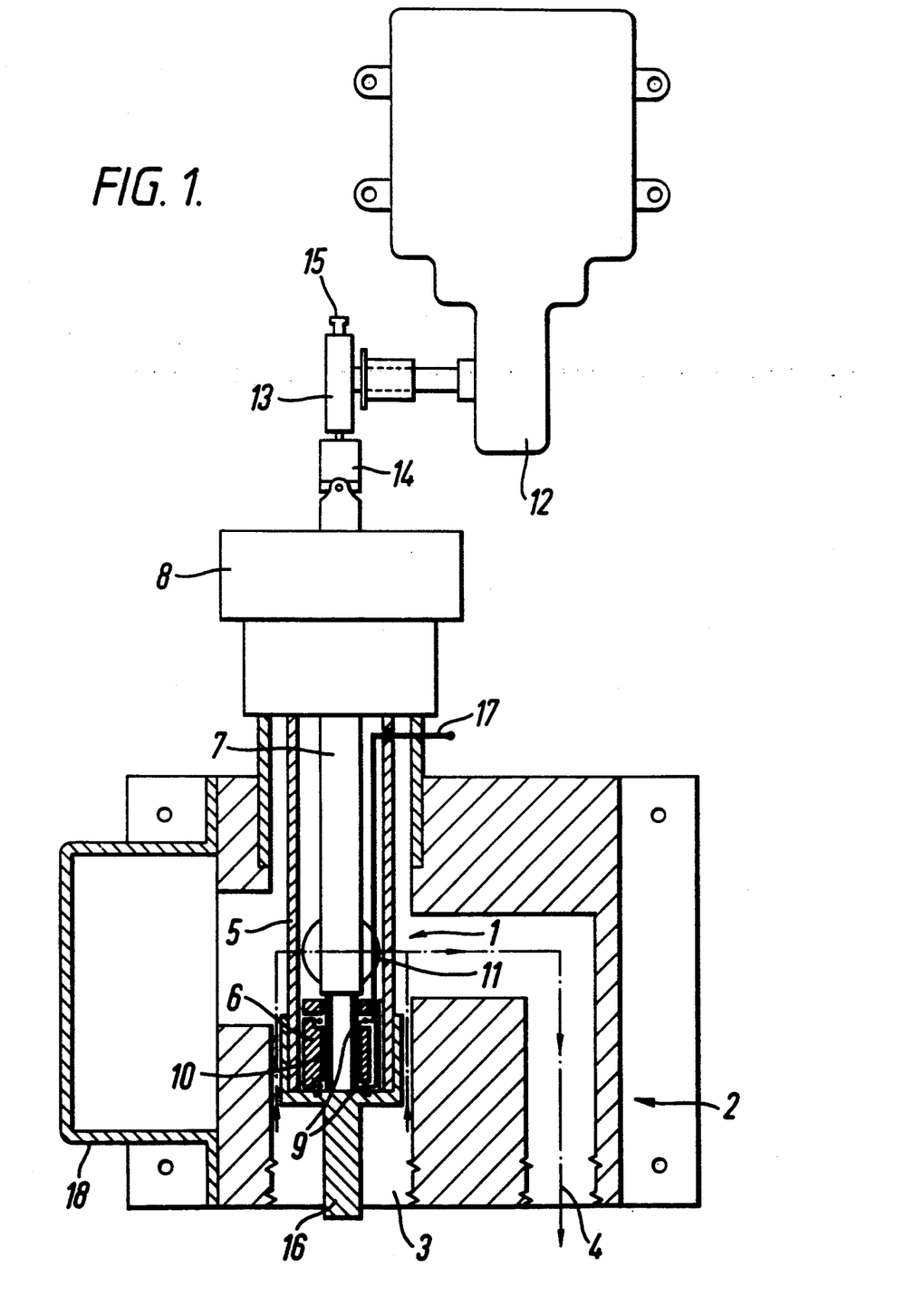
FIG. 1 is a part longitudinal cross-sectional view of a known SCD apparatus.

The basic elements of this known construction of SCD are an SCD cell 1 mounted in a fluid flow housing 2, the fluid flow housing 2 having a fluid inlet 3 and a fluid outlet 4, with a fluid flow passage extending between the inlet and outlet for conducting fluid flow through the housing. The SCD cell 1 comprises a cylindrical tubular casing 5 mounted with its lower end in the fluid opening 3, and with its opposite end projecting outside the housing 2. Mounted within the tubular casing 5 at its lower end is a piston-receiving member 6 in the form of a sleeve of insulating material having a central bore which receives the lower end of a reciprocatable piston 7 disposed coaxially within the tubular casing 5. The upper end of the piston 7 extends through a cap assembly 8 fixed to the outwardly projecting portion of the tubular casing 5. The piston-receiving member 6 carries a pair of annular electrodes 9 which are spaced apart along the axis of the piston, and there is an annular gap 10 between the lower end of the piston 7 received in the member 6, and the cylindrical surface of the bore in this member 6. The tubular casing 5 is formed with two diametrically opposed openings 11 through which fluid from the fluid-flow passage within the housing 2 can pass toward and from the bore of the member 6.

The piston is driven by a motor 12 coupled through an eccentric element 13 and a universal coupling 14 to the upper end of the piston. A sensor 15 detects the rotational position of the eccentric member 13 and thus the longitudinal position of the piston 7.

In use, the test fluid containing finely-divided particles is supplied to the inlet 3 and passes upwardly around the outside of a base cap 16 which closes off the lower end of the tubular casing 5, and generally follows the path of the chain-dashed arrow toward the outlet 4. As the motor 12 rotates, the lower end of the piston 7 reciprocates within the bore of the member 6. The upward travel of the piston draws fluid which has entered the casing 5 through the openings 11, through the annular gap 10 into the member 6. The downward stroke of the piston causes reverse flow of the fluid out of the member 6, thereby displacing an amount of fluid from within the tubular casing 5 back into the fluid flow path through the housing 2.

Each stroke of the piston causes relative movement between particles adhering to the inside wall of the member 6 and particles travelling axially in the annular gap, thus generating a signal across the electrodes 9, this signal being coupled to external measuring equipment by means of conductors 17.

The fluid under test thus passes up from the fluid inlet 3 through the annular gap between the upper portion of the cap 16 and the cylindrical wall of the inlet bore, and thence along a tortuous passage as indicated by the chain-dot lines to the outlet 4.

The above-described equipment has been used satisfactorily for process waters of moderate concentrations of suspended particles, the problem of accumulation of particles being alleviated by the attachment of an ultrasonic device 18 to the housing 5 to generate mechanical vibrations in the liquid.

It has been suggested that when dealing with fluids with above average particle size and/or concentration a partial filtering of a sample flow taken from the main fluid flow be performed and the filtrate be supplied to the SCD for monitoring. An indication of the concentration in the main flow is then obtained by processing the SCD output in accordance with the known filtering characteristics of the filter. However, this process is somewhat cumbersome and produces a certain time delay between the sampling from the main fluid flow and the generation of the detection output for that sample.

These problems arising from high concentration of particles are encountered in such applications as water purification, and the treatment of domestic sewerage, sludge, industrial fluids and industrial effluents.

The present invention seeks to alleviate, at least partly, this problem.

We have found that the constructional geometry within the housing has a significant effect upon the flow of large particles through the cell, and have developed an improved arrangement having constructional features leading to significant operational advantages over the arrangements known hitherto.

SUMMARY OF THE INVENTION

According to one aspect of the present invention there is provided a streaming current detector in which a piston is arranged to reciprocate in a bore of a piston-receiving member to cause test samples of a fluid containing charge-influencing particles suspended therein repeatedly to flow into and from said bore for the generation across electrodes spaced apart along the bore of signals representing a charge-related parameter of the fluid, characterised by means defining a passageway for conducting a main flow of the fluid from which the test samples are taken, across the open end of the bore through which said test samples enter and leave said bore, said passageway including a portion downstream of the position of said bore with respect to the fluid flow, in which the fluid level is raised so as to create a head for maintaining the passageway filled at said position of the bore.

According to another aspect of the invention there is provided a streaming current detector for use in determining a charge-related parameter in a system comprising a fluid containing charge-influencing particles suspended therein, the detector comprising:

a housing formed with a fluid-flow passageway for conducting a main flow of a said fluid to be tested through the housing, and a streaming current cell mounted to said housing for direct communication with said main fluid flow, said cell comprising a tubular casing extending across said passageway and having openings therein to permit the main flow of fluid to enter and to flow through said casing in a direction generally transverse its longitudinal axis, a piston-receiving member mounted coaxially in a part of said casing disposed to one side of the passageway and formed with a piston-receiving bore, a pair of detection electrodes mounted in said piston-receiving member, and exposed within and spaced apart along said piston-receiving bore, and a reciprocating piston arranged to reciprocate within said piston-receiving bore so as to repeatedly cause fluid from the main flow in said passageway to flow into and from said bore and thereby generate electrical signals across said electrodes by the streaming current effect, said passageway including a portion downstream of the position of said casing with respect to the fluid flow, in which the fluid level is raised so as to create a head for maintaining the passageway filled at said position of the casing.

The housing preferably comprises a block formed with a fluid entry port and a fluid exit port for said main fluid flow, an enclosed bore extending across the block between said fluid entry and exit ports, and a transverse bore intersecting and crossing said enclosed bore, said tubular casing being fixed within said transverse bore with its said openings aligned with and along the enclosed bore.

The block preferably has opposed end faces in parallel planes, each of said fluid entry and exit ports being formed in a respective one of said end faces, and first opposite side faces extending in parallel planes between said end faces, the transverse bore opening onto one of said side faces for insertion of said casing into the block during assembly, and said piston extending through a piston bore which extends coaxially from said transverse bore and out of said block at a piston-receiving opening formed in the other of said side faces.

Said head-creating portion of the passageway may comprise a step in said enclosed bore at a position downstream of the intersection with the transverse bore, the fluid exit port being at a higher level than the fluid entry port.

The opening of said transverse bore onto said one of said side faces is sealed off by the configuration of the base end of the tubular casing, the piston-receiving element fitted within said casing and a plug element which closes the lower end of the piston-receiving bore.

The block may be formed with a further bore extending from an opening on one of a pair of second opposite side faces extending in parallel planes perpendicular to the planes of the first opposite side faces and of the end faces, said further bore intersecting said enclosed bore, said tubular casing having a further opening in communication with said further bore. A sonic cleaning device, such as an ultrasonic transducer, may be mounted on said block over said opening on said second side face for generating mechanical vibrations in the fluid in the block to inhibit agglomeration of said suspended particles on or around surfaces of the streaming current cell.

As mentioned before, the detector of the present invention is particularly suitable for use in applications where there is a very high concentration of solid particles in suspension, e.g. in sewerage treatment. In these applications, for which the conventional SCD would be totally unusable, the through-flow configuration avoids rapid clogging with accumulated solids. Nevertheless, the high solid concentrations in such applications could lead to eventual clogging. In a further aspect of the invention, a system for fluid treatment which uses a through-flow SCD also includes an arrangement for selectively flushing the SCD through with a cleaning liquid, e.g. clean water, to displace and remove accumulations of particles from the interior of the SCD.

According to this aspect of the invention there is provided a system for treating a supplied fluid which contains charge-influencing particles suspended therein in relatively high concentration, said system including means for adding flocculant to the supplied fluid to cause the particles to agglomerate, means for removing the agglomerated particles from the fluid, and a streaming current detector for receiving test fluid obtained from the supplied fluid to provide a test output for use in controlling the amount of flocculant added to the supplied fluid, the streaming current detector including a piston arranged to reciprocate in a bore of a piston-receiving member to cause test samples of the test fluid repeatedly to flow into and from said bore for the generation across electrodes spaced apart along the bore of signals representing a charge-related parameter of the test fluid, and means defining a passageway for conducting a main flow of the test fluid across the open end of the bore through which said test samples enter and leave said bore, the system further including means for selectively cleaning said streaming current detector by supplying to said passageway a flow of cleaning liquid instead of the test liquid.

The test fluid which the streaming current detector receives may be filtrate obtained in the process of removal of the agglomerated particles from the supplied fluid. For example, the sludge formed by the fluid with agglomerated particles may be supplied to a mechanical dewatering device such as a belt filter press in which said sludge is progressively squeezed between two filter belts which pass over a succession of rotary rollers, the filtrate falling from the belts being collected in a trough in the base of the machine and pumped from this trough to the streaming current detector as the test fluid. In the disclosed embodiment, a valve arrangement between the belt filter press and the streaming current detector is actuable by a central control to cause clean water to be pumped periodically into and through the passageway of the detector. In the embodiment, the clean water is also pumped along a test fluid line leading from the trough of the belt filter press to clean this line.

Thus, in this aspect automation of the dosing of sewerage or industrial sludge using an SCD is made possible because the configuration of the SCD of the invention allows the periodic cleaning by throughflushing. Conventional SCD's cannot be used in this way as they require dismantling in order to be cleaned. The central control is preferably adapted to perform the SCD cleaning operation at regular intervals during use. In order to maintain proper operation of the system during the SCD cleaning cycle, the central control is preferably arranged to hold the latest test output value for control of the flocculation dosing until the filtrate from the belt press again reaches the SCD after return of the valve following completion of said cleaning cycle.

Preferably, the central controller is also adapted to provide a suitable shut-down and restart control when the belt filter press or other treatment apparatus is stopped for any reason, e.g. manually for cleaning and maintenance, or automatically under alarm conditions, and is subsequently restarted.

When the machine is stopped, the operation of the dosing equipment is suspended, but the dosing pump is turned to manual control and is held at its previous setting, awaiting restart of the equipment. On restart, the controller allows the equipment to operate for a time at said previous setting and thereby stabilize, and then reverts to automatic control.

The central controller is preferably also adapted to selectively switch the system from the automatic control mode using the SCD signal to at least one other mode which uses some other form of control signal, generated automatically or manually; this facility affords flexibility of operation and permits selection of control mode according to the operating conditions of the equipment.

Preferred embodiments of the invention will now be described by way of example with reference to FIGS. 2 to 4 of the accompanying drawings.

DESCRIPTION OF THE PREFERRED EMBODIMENTS

Figure 2:
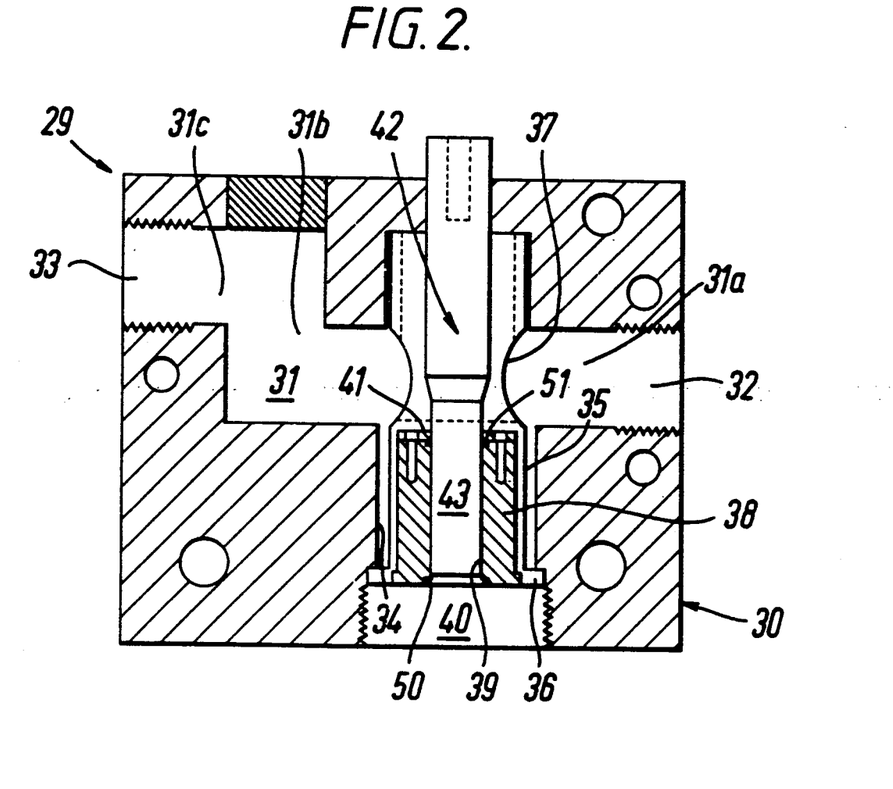
FIG. 2 is a part longitudinal cross-section through a part of a SCD apparatus in accordance with the present invention.
Figure 3:
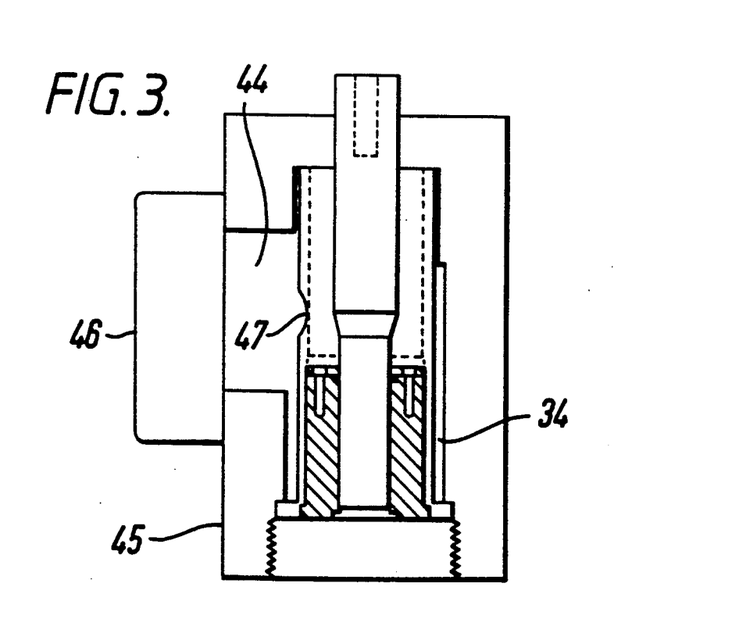
FIG. 3 is a part transverse cross-sectional view through the part of the SCD shown in FIG. 2.

For the sake of clarity, FIGS. 2 and 3 show the part of the SCD incorporating features of distinction in accordance with the present invention; a number of other essential components, such as the arrangement for piston reciprocation, are omitted as these can be the same as in the known devices.

Figure 2A:
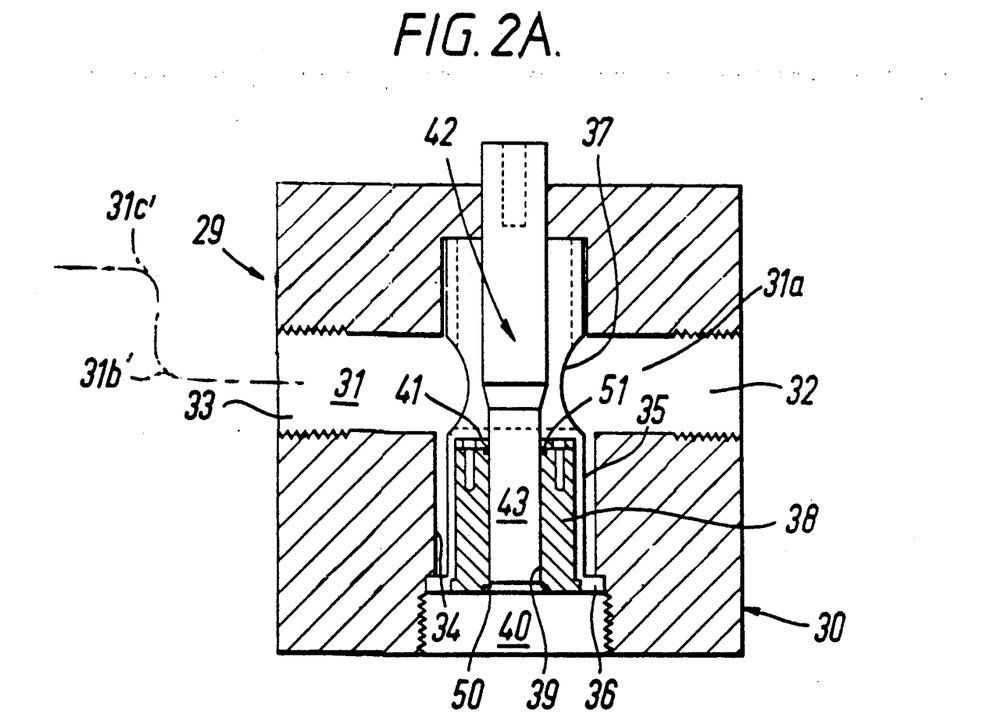
FIG. 2A is a diagram similar to FIG. 2 but showing a modification.

The SCD 29 illustrated in FIGS. 2 and 3 includes a generally cuboid housing 30 formed with a main flow-through passageway 31 extending across and within the housing 30 from a fluid entry port 32 to a fluid exit port 33. The passageway 31 has a main straight portion 31a leading inwardly from the inlet port 32, and an upward step consisting of two right-angled bends 31b, 31c leading the passageway upwardly and then horizontally to the outlet port 33. This arrangement ensures that the outlet 33 is higher than the inlet 32 to ensure a minimum head of fluid pressure in the region of the SCD cell. This, in turn, ensures that the main portion 31a of the passageway is in use always filled with the fluid supplied to the port 32 for proper sampling by the SCD cell described below. This step formed within the housing 30 may be replaced by an external upward step provided in the downstream pipework connected to the outlet port 33, as shown in FIG. 2A wherein the pipework external to housing 30 is schematically shown by the dot-dash course of the pipework centerline, containing a step-up bend 31b' and a further bend 31c' for horizontal redirection of outlet flow.

The housing 30 is also formed with a transverse bore 34 extending upwardly from a base face of the housing block, this transverse bore 34 intersecting and crossing the straight portion 31a of the fluid passageway. Fixedly disposed within this transverse bore 34 is the SCD cell which comprises a cylindrical tubular casing 35 formed at its lower end with a flange 36 which locates against an annular shoulder formed in the transverse bore 34. The part of the casing 35 exposed within the passageway 31 is formed with two diametrically opposed openings 37 of the same diameter as the passageway, these openings 37 being aligned with and along the axis of the passageway. In this arrangement, a flow of fluid supplied to the inlet port 32 can pass along the passageway 31 unimpeded by the presence of the tubular casing 35.

A cylindrical piston-receiving element 38 of electrically insulating material is fixed coaxially within the base part of the casing 35 which is disposed in the part of the transverse bore 34 to the lower side of the passageway 31. This member 38 has a cylindrical piston-receiving bore 39 which is closed at the base end of the member 38 by a threaded plug or cap (not shown) screwed into the threaded opening 40 of the bore 34. An annular electrode 50 is recessed into the inner wall of the piston-receiving bore at its lower end and an upper fixing ring 41 serves to locate a similar upper annular electrode 51. A piston 42 driven by a reciprocating drive (not shown) is located coaxially within the casing 34 so that its lower end 43 continuously and repetitively reciprocates within the bore 39. The diameter of the lower portion of the piston is slightly less than the inner diameter of the bore 39 so as to form a narrow annular gap providing the necessary clearance to achieve the streaming current effect described earlier in relation to the known arrangement of FIG. 1.

As can be seen in FIG. 3, the housing 30 is also formed with a further transverse bore 44 extending from a side face 45 of the cuboid housing 30 to intersect the transverse bore 34 and the fluid flow passageway 31. The tubular casing 35 is formed with an opening 47 facing the further transverse bore 43. A sonic device, such as an ultrasonic transducer 46 may be mounted on the side face 45 so as to generate mechanical vibrations in the fluid which, in use, fills the passageway 31 and bore 44 in the housing 30 so as to inhibit the accumulation of particles on the various surfaces of the SCD cell, in a known manner.

The stroke of the piston is such that at its lowest point the lower end of the piston lies adjacent the cap plug 40, as shown in FIGS. 2 and 3, and such that it remains at all times within the bore 39. As in the known arrangement the upward thrust of the piston acts to draw particle-bearing liquid from the main flow passageway extending through the openings 37, into the member 38 downwardly by way of the narrow annular gap, while the downward thrust acts to expel the liquid sample and return it to the main flow.

It has been found that with the above geometrical configuration within the housing 30 a very substantial through-flow of fluid can be achieved, and the SCD operates continuously and reliably even at very high particle concentrations.

With this construction of SCD, therefore, it is no longer necessary when dealing with such fluids to carry out an initial filtration; the fluid can simply be pumped directly into the SCD so that a direct and immediate monitoring of the particle concentrations can be achieved. Conventional SCD constructions, such as the one described earlier with reference to FIG. 1, would be unusable at high particle concentrations, since particle accumulations would very quickly build up on the surfaces defining the restricted flow path for the test fluid, and since complete dismantling would be required each time the cell had to be cleaned.

The structure of the SCD cell described above in accordance with the invention, however, permits cleaning to be carried out by periodically forcing clean water along the main passageway through the device to flush out particle accumulations. Such a cleaning operation, involving interruption of the flow of a test liquid through the SCD, and connection to a clean water source, can be carried out at regular intervals, the frequency with which the cleaning operation is performed being predetermined according to the known characteristics of the particle suspension to be tested.

Figure 4:
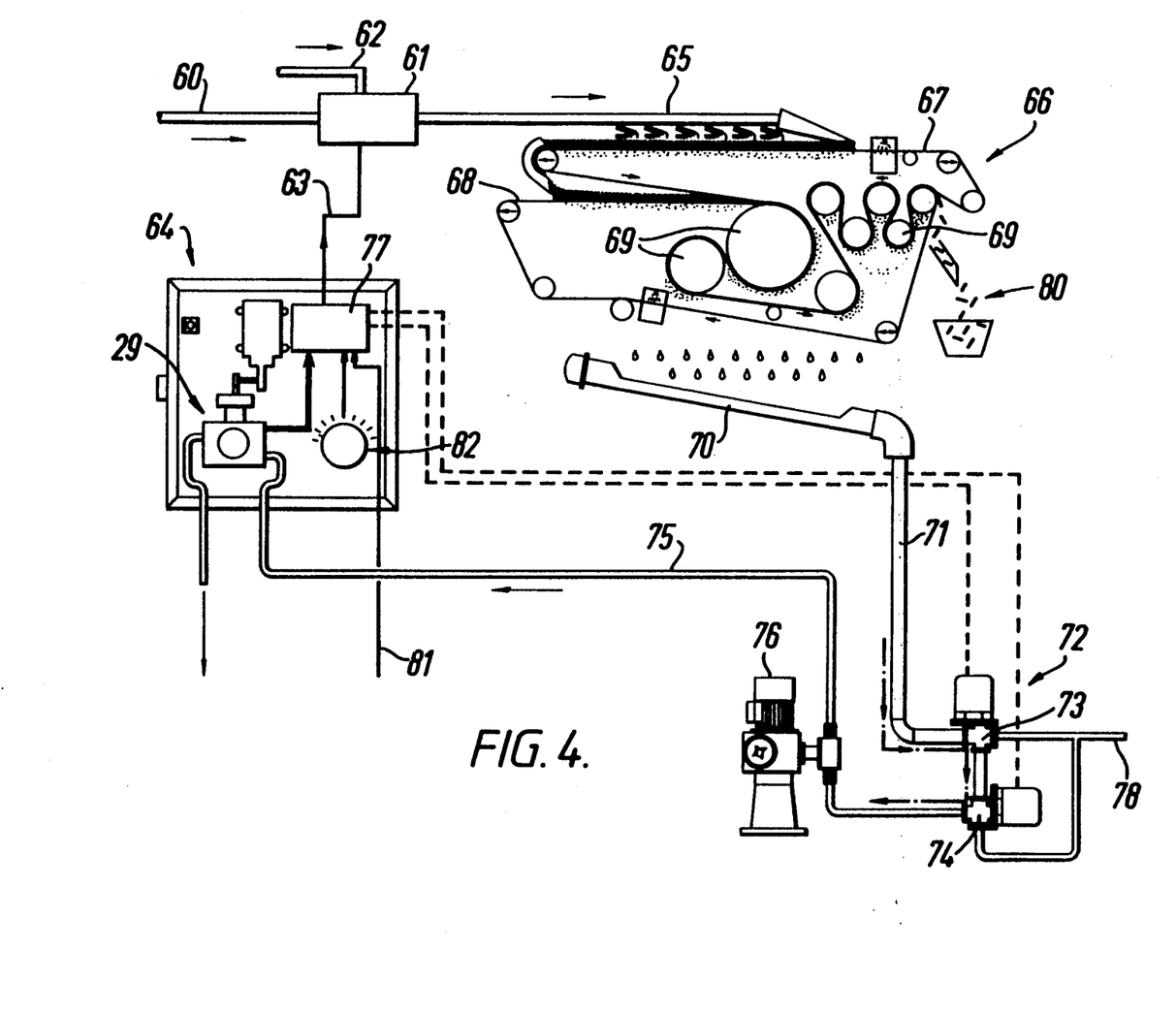
FIG. 4 is a schematic diagram of a fluid treatment system incorporating automatic dosing control using an SCD, in accordance with the present invention.

An example of a fluid treatment system in accordance with the invention using a through-flow SCD is illustrated in FIG. 4 of the drawings. The illustrated system is one which treats sewerage or industrial effluent in slurry form to extract the solids. In this system, a thin slurry comprising a high concentration of finely divided particles in aqueous suspension is supplied along a supply line 60 to a mixing or dosing station 61 where it is mixed with a controlled supply of polyelectrolyte flocculant supplied along a feed line 62. The addition of the polyelectrolyte to the slurry is controlled by a suitable valve arrangement, and the amount of polyelectrolyte added is controlled by a control signal supplied to the mixing station along a control line 63 from a central control unit 64, to be described later. The mixed slurry and polyelectrolyte pass along another supply pipe 65 to a separation station in the form of a filtration machine 66, for example a belt filter press. Intermixing of the slurry and polyelectrolyte in the pipe 65 causes agglomeration of the waste particles into lumps suitable for separation filtration. The degree of agglomeration depends upon the rate of addition of the polyelectrolyte, and at an optimum rate of polyelectrolyte addition the concentration of unagglomerated particles is minimum.

In the filtration machine the lumps are removed by a suitable process; in the case of a belt filter press as shown the material emerging from the end of the supply line 65 is deposited onto a moving filter belt 67, and the primary filtrate carrying the unbound particles drains through the belt. The solids remaining on the belt are then sandwiched between two moving belts 67, 68, and as these belts pass under high tension around a succession of rotating rollers 69, further filtrate is removed and drains, along with the primary filtrate, into a drainage trough 70 provided in the base of the machine. After the belts emerge from the roller system, they separate and the nearly-dry solids 80 are removed and can then be disposed of or used as appropriate.

As mentioned earlier, the concentration of particles in the filtrate provides a measure of the efficiency of flocculation and can be used for the derivation of a control signal for use in the mixing station 61. A small proportion of the filtrate is supplied along a primary fluid test line 71 to a valve arrangement 72 which consists of two three-way valves 73, 74. In the normal operative position of these valves, the filtrate passes along the path illustrated by chain dot line to a secondary fluid test line 75, along which it is pumped by a feed pump 76 to the inlet port 32 of an SCD 29 as described earlier, this SCD 29 comprising a part of the central control unit 64. The control unit 64 also includes a display and control panel (not shown) including various necessary display and warning lights, control knobs etc, and control electronics 77 to provide control over the system as described below. For the sake of brevity, full constructional details of the control electronics used in the control unit are not described herein. It is believed that the design of a practical unit lies within the competence of an ordinary person skilled in the art, given the required mode of operation described herein.

Each of the two three-way valves 73, 74, is also connected to a fresh water supply line 78; the first valve 73 is switchable to connect the fresh water supply to the primary test fluid line 71, and the second valve 74 is switchable to connect the fresh water supply to the secondary test fluid line 75.

In the normal positions of the valves, the filtrate is supplied to the SCD 29 which operates as described earlier to derive a signal using the streaming current effect. This signal is supplied to the electronic control 77 which derives a feedback control signal fed to the mixing station 61 on the line 63. At predetermined periodic intervals the electronic control 68 initiates a cleaning cycle, in which the two valves 73, 74 are switched so as to supply fresh water from supply line 78 both along the primary test fluid line 71 to clear particle accumulations therefrom, and along the secondary test fluid line 75 to the SCD 29. The fresh water is supplied under high pressure and flushes through the passageway 31 in the SCD housing 30, removing any accumulations of particles which may have built up on the passageway walls. Continued reciprocation of the piston 42 during the cleaning cycle ensures that clean water is also repetitively pumped into and out of the bore 39 in the piston-receiving element 38. In this way, the SCD can be thoroughly cleansed. Continued control over the flocculent mixing during the SCD cleaning cycle would, of course, result in incorrect dosing; to avoid this, the electronic control is programmed to hold the control signal on line 63 throughout the cleaning cycle at its level existing immediately prior to initiation of the cleaning cycle. After a predetermined period of flushing with clean water, the two valves 73, 74 are switched back to their normal position, and the supply of the filtrate to the SCD is resumed. The control signal is held after this switching of the valves for a predetermined period calculated according to the known filtrate flow rate and dimensions of pipework to ensure resumption of feedback control only after filtrate again reaches the SCD.

The fluid which passes through the SCD 29, whether this be filtrate from the filtration apparatus 66 or flush-through water in the cleaning mode, flows to drain.

The filtration machine will normally be provided with controls which enable it to be started and stopped in various ways, either manually by the operator or automatically under certain conditions. The control electronics 77 may therefore also be programmed to provide a suitable shut-down and restart control procedure. When the filtration machine is stopped, a signal is sent along line 63 to suspend the dosing of the slurry, and to render the mixing station 61 manually controllable by means of a manual control 82 provided on the controller 64. The setting of the dosing pump just before shut-down is held under manual control, awaiting restart. When the filtration machine is restarted, the controller 77 will maintain operation under manual control at the held setting for a given time to allow the system to restabilize, and will then revert to automatic control using the SCD signal.

Although the system will normally be operated under SCD automatic control, under certain operating conditions other forms of automatic/manual control may be more appropriate. To allow for this, the control electronics is provided with the facility for automatic or manual switching out of the SCD automatic control mode to another mode using some other form of control signal, for example a remotely generated signal supplied on a line 81. For example, a feedback control signal from a moisture monitoring device which in turn would be measuring the residual moisture in the final nearly dry solids 80 and utilised to update the SCD controller set point.

What is claimed is:

1. A streaming current detector in which a piston is arranged to reciprocate in the upwardly open ended bore of a piston-receiving member to cause test samples of a fluid containing charge-influencing particles suspended therein repeatedly to flow into and from said bore for the generation across electrodes spaced apart along the bore of signals representing a charge-related parameter of the fluid, characterized by means defining a passageway for conducting a main flow of the fluid from which test samples are taken, said main-flow passageway being across and above and communicating with the open end of the bore through which test samples enter and leave said bore, said passageway including a step portion downstream of the passageway crossing above said bore, said step portion locally elevating said passageway above the level at which the passageway communicates with the open end of the bore, whereby the fluid level may be raised to create a head for maintaining the passageway in filled communication with the open end of the bore.

2. A streaming current detector for use in determining a charge-related parameter in a fluid-flow system wherein the fluid contains charge-influencing particles suspended therein, the detector comprising:
   a housing formed with a fluid-flow passageway for conducting fluid to be tested through the housing, said housing comprising a block formed with a fluid entry port, a fluid exit port, an enclosed bore extending across the block between said fluid entry port and said fluid exit port and defining said fluid-flow passageway and a transverse bore intersecting and crossing said enclosed bore, and
   a streaming current cell mounted in said housing for direct communication with said fluid-flow passageway,
   said cell comprising a tubular casing having a longitudinal axis extending across said fluid-flow passageway, openings therein to permit fluid flowing along said fluid-flow passageway to enter and to flow through said casing in a direction generally transverse said longitudinal axis, said tubular casing being fixed within said transverse bore with said openings aligned with and along the enclosed bore,
   a piston-receiving member disposed to one side of the fluid-flow passageway and formed with a piston-receiving bore, said piston-receiving member being mounted coaxially in said casing,
   a pair of detection electrodes mounted in said piston-receiving member, and exposed within and spaced apart along said piston-receiving bore,
   and a reciprocating piston within said piston-receiving bore, said piston being mounted for reciprocation with said piston-receiving bore so as repeatedly to cause fluid in said fluid-flow passageway to flow into and from said piston-receiving bore and thereby generate electrical signals across said detection electrodes by the streaming current effect, said fluid-flow passageway comprising a step in said enclosed bore at a position downstream of the intersection with the transverse bore with respect to the fluid-flow, the fluid exit port being at a higher level than the fluid entry port so as to create a head for maintaining the fluid-flow passageway filled at said intersection.

3. A streaming current detector for use in determining a charge-related parameter in a system comprising a fluid containing charge-influencing particles suspended therein, the detector comprising:
   a housing formed with a fluid passageway for conducting fluid to be tested through the housing, said housing comprising a block formed with a fluid entry port, a fluid exit port, an enclosed bore extending across the block between said fluid entry port and said fluid exit port and defining said fluid-flow passageway, opposed end faces in parallel planes, each of said fluid entry and exit ports being formed in a respective one of said end faces, first and second opposite side faces extending in respective first and second parallel planes between said end faces, said first side face having a piston-receiving opening, a transverse bore intersecting and crossing said enclosed bore, the transverse bore opening onto said second side face, and a first piston-receiving bore axially aligned with and communicating with said transverse bore and extending from said transverse bore to said piston-receiving opening, and a streaming current cell mounted in said housing for direct communication with said fluid-flow passageway, said cell comprising a tubular casing having a longitudinal axis extending across said fluid-flow passageway, openings therein to permit fluid flowing along said fluid-flow passageway to enter and to flow through said casing in a direction generally transverse said longitudinal axis, said tubular casing being fixed within said transverse bore with said openings aligned with and along the enclosed bore, a piston-receiving member disposed to one side of the fluid-flow passageway and formed with a second piston-receiving bore axially aligned with said first piston-receiving bore, said piston-receiving member being mounted coaxially in said casing, a pair of detection electrodes mounted in said piston-receiving member, and exposed within and spaced apart along said second piston-receiving bore, and a reciprocating piston within said first and second piston-receiving bores, said piston being mounted for reciprocation within said first and second piston-receiving bores so as repeatedly to cause fluid in said fluid-flow passageway to flow into and from said second piston-receiving bore and thereby generate electrical signals across said detection electrodes by the streaming current effect, said fluid-flow passageway including a portion downstream of the intersection of said enclosed and transverse bores with respect to the fluid flow, which is raised relative to the level of the enclosed bore at said intersection so as to create a head for maintaining the passageway filled at said intersection.

4. A streaming current detector according to claim 3, wherein the tubular casing has a base end and the second piston-receiving bore has a lower end and the opening of said transverse bore onto said second side face is sealed off by a plug or cap element which abuts the base end of the tubular casing and closes the lower end of the second piston-receiving bore therein.

5. A streaming current detector according to claim 3, wherein the block is formed with third and fourth opposite side faces extending in respective third and fourth parallel planes perpendicular to the first and second planes of the first and second opposite side faces and of the end faces, and a further bore extending from an opening on one of said third and fourth side faces, said further bore intersecting said enclosed bore, said tubular casing having a further opening in communication with said further bore, and wherein a sonic cleaning device, such as an ultrasonic transducer, is mounted on said block over said opening on said one of said third and fourth side faces for generating mechanical vibrations in the fluid in the block to inhibit agglomeration of said suspended particles on or around surfaces of the streaming current cell.

6. A system for treating a supplied fluid which contains charge-influencing particles suspended therein in relatively high concentrations, said system including means for adding flocculant to the supplied fluid to cause charge-influencing particles therein to agglomerate, a filtration machine for separating the agglomerated particles from the fluid, and a streaming current detector for receiving test fluid obtained from the supplied fluid to provide a test output for use in controlling the amount of flocculant added to the supplied fluid, the streaming current detector including a piston arranged to reciprocate in a bore of a piston-receiving member to cause test samples of the test fluid repeatedly to flow into and from said bore for the generation across electrodes spaced apart along the bore of signals representing a charge-related parameter of the test fluid, and means defining a passageway for conducting a main flow of the test fluid across an open end of the bore through which said test samples enter and leave said bore, the system further including means for selectively cleaning said streaming current detector by supplying to said passageway a flow of cleaning liquid instead of the test fluid, and means for conveying filtrate from said filtration machine to said streaming current detector as the test fluid.

7. A system according to claim 6 wherein said cleaning means comprises valve means switchable between a first valve state for conveying test fluid toward said streaming current detector and a second valve state for blocking the test fluid flow and for conveying cleaning fluid to said streaming current detector.

8. A system according to claim 7, further including control means for controlling the system, said control means comprising means for storing a held signal representative of one of said signals representing a charge-related parameter existing immediately prior to actuation of said means for supplying cleaning liquid to said passageway and for controlling the addition of the flocculant in response to said held signal during said cleaning, thereby to maintain the operation of the system during said cleaning.

9. A system according to claim 6, wherein the streaming current detector generates a concentration signal representative of a concentration of charge-influencing particles in a fluid supplied thereto, and wherein the system further comprises means for detecting cessation of operation of said filtration machine, means for detecting restart of the system and means for storing a held signal representative of the value of said concentration signal immediately prior to detection of cessation, said means for adding flocculant to the supplied fluid being responsive to said held signal for a predetermined period after detection of restart and thereafter being responsive to said concentration signal.

10. A system according to claim 9, wherein means is provided for manual operation of said system for said predetermined period after detection of said restart, said means for adding flocculant being responsive to said concentration signal thereafter.

11. A system for treating a supplied fluid which contains charge-influencing particles suspended therein in relatively high concentrations, said system including means for adding flocculant to the supplied fluid to cause charge-influencing particles therein to agglomerate, a filtration machine, a streaming current detector for receiving test fluid obtained from the supplied fluid to provide a concentration signal representative of a concentration of charge-influencing particles in a fluid supplied thereto, and control means for controlling said means for adding flocculant in accordance with said concentration signal, the system further comprising means for detecting cessation of operation of said filtration machine, means for detecting restart of the system and means for storing a held signal representative of the value of said concentration signal immediately prior to detection of said cessation, said means for adding flocculant to the supplied fluid being responsive to said held signal for a predetermined period after detection of restart, thereafter being responsive to said concentration signal and means for conveying filtration from said filtration machine to said streaming current detector as the test fluid.

12. A system according to claim 11, wherein means is provided for manual operation of said system for said predetermined period after detection of said restart.

13. As an article of manufacture, a unitary streaming-current cell assembly adapted to series connection in a line of continuously flowing liquid containing a suspension of charge-influencing particles, said article comprising a prismatic block with a flow-through passageway of substantially uniform cross-section extending generally horizontally between inlet and outlet ports at opposed sides of said block, said block having a cell bore which intersects said passageway on a vertical axis, an annular cell member have a cylindrical piston-receiving bore and retained in the cell bore beneath cell-bore intercept with said passageway a pair of detection electrodes mounted in said annular cell member, and exposed within and spaced apart along said piston-receiving bore, and a reciprocating piston within said piston-receiving bore, said piston being mounted for reciprocation so as repeatedly to cause fluid in said flow-through passageway to flow into and form said piston-receiving bore and thereby generate electrical signals across said detection electrodes by the steaming current effect, said reciprocating piston being guided by the cell bore above cell-bore intercept with said passageway and having a cylindrical lower end in concentric clearance relation with the piston-receiving bore of said annular cell member said passageway including a head-creating formation connected to or in the vicinity of said outlet port, said head-creating formation being at vertical offset from the level of said passageway at intercept with said cell bore.

14. The article of claim 13, in which said cell bore include a cylindrical counterbore which extends continuously from the bottom of said block to at least an elevation above intercept with said passageway, said counterbore being of greater sectional area than the sectional area of said passageway, a tubular casing removably fitted to said counterbore above and below intercept with said passageway, said counterbore fixedly retaining said annular cell member and said counterbore having aligned openings which are aligned with and of effectively the open sectional area of said passageway, whereby to offer effectively unimpeded continuous flow in said passageway.

15. The article of claim 13, in which said passageway extends on the same single horizontal alignment between each of said ports and passageway intercept with said cell bore.

16. A system for treating a supplied fluid which contains charge-influencing particles suspended therein in relatively high concentrations, said system including means for adding flocculant to the supplied fluid to cause charge-influencing particles therein to agglomerate, a filtration machine for separating the agglomerated particles from the fluid, and a streaming current detector for receiving test fluid obtained from the supplied fluid to provide a test output for use in controlling the amount of flocculant added to the supplied fluid, the streaming current detector including a piston arranged to reciprocate in a bore of a piston-receiving member to cause test samples of the test fluid repeatedly to flow into and from said bore for the generation across electrodes spaced apart along the bore of signals representing a charge-related parameter of the test fluid, and means defining a passageway for conducting a main flow of the test fluid across the open end of the bore through which said test samples enter and leave said bore, and means for conveying filtrate from said filtration machine to said streaming current detector as the test fluid.

* * * * *